(12) United States Patent
Elfring et al.

(10) Patent No.: US 11,255,469 B2
(45) Date of Patent: Feb. 22, 2022

(54) SEALING DEVICE AND MEDICAL DEVICE WITH AT LEAST ONE SEALING DEVICE

(71) Applicant: Drägerwerk AG & Co. KGaA, Lübeck (DE)

(72) Inventors: Robert Elfring, Kassel (DE); Christian Jäke, Hamburg (DE); Thomas Martin, Lübeck (DE)

(73) Assignee: Drägerwerk AG & Co. KGaA, Lübeck (DE)

(*) Notice: Subject to any disclaimer, the term of this patent is extended or adjusted under 35 U.S.C. 154(b) by 294 days.

(21) Appl. No.: 16/161,656

(22) Filed: Oct. 16, 2018

(65) Prior Publication Data

US 2019/0113159 A1   Apr. 18, 2019

(30) Foreign Application Priority Data

Oct. 17, 2017   (DE) .................... 10 2017 009 674.0

(51) Int. Cl.

| | |
|---|---|
| *F16L 3/04* | (2006.01) |
| *F16L 19/02* | (2006.01) |
| *F16L 5/10* | (2006.01) |
| *A61M 16/08* | (2006.01) |
| *F16L 3/01* | (2006.01) |
| *F16L 19/04* | (2006.01) |

(52) U.S. Cl.
CPC ......... *F16L 19/0225* (2013.01); *A61M 16/08* (2013.01); *A61M 16/0875* (2013.01); *F16L 3/01* (2013.01); *F16L 3/04* (2013.01); *F16L 5/10* (2013.01); *F16L 19/043* (2013.01); *F16L 2201/20* (2013.01); *F16L 2201/44* (2013.01)

(58) Field of Classification Search
CPC ......... F16L 39/06; F16L 2201/44; F16L 3/04; F16L 2201/30; F16L 2201/20; F16L 5/02; A61M 16/0463
USPC .............................. 285/13, 14; 604/513, 163
See application file for complete search history.

(56) References Cited

U.S. PATENT DOCUMENTS

| | | | | |
|---|---|---|---|---|
| 315,788 A | * | 4/1885 | Hunter | F16L 23/167 285/13 |
| 321,905 A | * | 7/1885 | Lutomski | F16L 23/167 285/13 |

(Continued)

FOREIGN PATENT DOCUMENTS

| | | |
|---|---|---|
| DE | 10355213 A1 | 6/2005 |
| DE | 102010048518 A1 | 4/2012 |

(Continued)

*Primary Examiner* — David Bochna
(74) *Attorney, Agent, or Firm* — McGlew and Tuttle, P.C.

(57) ABSTRACT

A gas-tight sealing device (10) encloses at least one part of a coupling element (12) as well as at least one section of a line element (14) connected to the coupling element (12). The the gas-tight sealing device (10) comprises a sealing device portion or wall (11) that adjoins a first sealing point and a second sealing point (16, 18). The sealing device portion or wall (11) extends around, in a gas-tight manner, the line element (14) and the coupling element (12) or a wall (20), or a further line element, in or at which the coupling element (12). The gas-tight sealing device (10) encloses a volume defined by the geometry of the sealing device portion (11) in a gas-tight manner between the first sealing point (16) and the second sealing point (16, 18).

20 Claims, 4 Drawing Sheets

(56) References Cited

U.S. PATENT DOCUMENTS

| | | | | |
|---|---|---|---|---|
| 333,412 A * | 12/1885 | Hoeveler | ............... | F16L 23/167 |
| | | | | 285/13 |
| 345,463 A * | 7/1886 | Verver | ................... | F16L 23/167 |
| | | | | 285/13 |
| 378,544 A * | 2/1888 | Ells | ....................... | F16L 23/167 |
| | | | | 285/13 |
| 425,369 A * | 4/1890 | Cowell | ................. | F16L 23/167 |
| | | | | 285/13 |
| 1,834,102 A * | 12/1931 | McCalley | .............. | F16L 13/122 |
| | | | | 285/148.8 |
| 3,894,540 A * | 7/1975 | Bonner, Jr. | ........ | A61M 25/0111 |
| | | | | 604/171 |
| 3,991,762 A * | 11/1976 | Radford | ............ | A61M 16/0463 |
| | | | | 604/119 |
| 4,691,702 A * | 9/1987 | Chantzis | ............ | A61M 16/0463 |
| | | | | 128/207.16 |
| 5,336,193 A * | 8/1994 | Rom | ................... | A61M 25/0111 |
| | | | | 206/364 |
| 5,368,017 A * | 11/1994 | Sorenson | .......... | A61M 16/0463 |
| | | | | 128/200.26 |
| 6,062,605 A * | 5/2000 | Goshima | ............ | F16L 19/0206 |
| | | | | 285/13 |
| 6,080,138 A * | 6/2000 | Lemke | .............. | A61M 25/0612 |
| | | | | 128/919 |
| 6,185,876 B1 | 2/2001 | Kummerfeld et al. | | |
| 6,602,219 B2 * | 8/2003 | Madsen | ............ | A61M 16/0463 |
| | | | | 604/27 |
| 6,827,707 B2 * | 12/2004 | Wright | ................... | A61M 25/02 |
| | | | | 604/174 |
| 6,893,428 B2 * | 5/2005 | Willemstyn | ......... | A61M 39/165 |
| | | | | 604/163 |
| 7,824,361 B2 * | 11/2010 | Luzbetak | ................ | A61M 1/06 |
| | | | | 604/74 |
| 7,963,565 B2 * | 6/2011 | Suter | .................... | A61C 19/002 |
| | | | | 285/4 |
| 9,413,152 B2 | 8/2016 | Fritz et al. | | |
| 10,682,507 B2 * | 6/2020 | Helm | .................... | A61M 25/02 |
| 2011/0106014 A1 * | 5/2011 | Helm, Jr. | ............... | A61M 25/02 |
| | | | | 604/178 |
| 2014/0231133 A1 | 8/2014 | Fritz et al. | | |
| 2016/0169427 A1 * | 6/2016 | Holtby | ................ | F16L 55/1715 |
| | | | | 285/13 |
| 2019/0216991 A1 * | 7/2019 | Locke | .................... | A61L 31/146 |
| 2019/0298950 A1 * | 10/2019 | Einav | ............ | A61M 16/0456 |

FOREIGN PATENT DOCUMENTS

| | | | | |
|---|---|---|---|---|
| DE | 102012004249 A1 | 9/2013 | | |
| DE | 102012018697 B3 | 3/2014 | | |
| DE | 102013202614 A1 | 8/2014 | | |
| FR | 2862736 B1 | 5/2005 | | |
| GB | 2107809 A | * | 5/1983 | ............. F16L 55/07 |

* cited by examiner

SEALING DEVICE AND MEDICAL DEVICE WITH AT LEAST ONE SEALING DEVICE

CROSS REFERENCE TO RELATED APPLICATIONS

This application claims the benefit of priority under 35 U.S.C. § 119 of German Application 10 2017 009 674.0, filed Oct. 17, 2017, the entire contents of which are incorporated herein by reference.

TECHNICAL FIELD

The present invention pertains to a connection point between a coupling element and a line element connected to the coupling element as well as to a device for sealing the connection point (sealing device). The coupling element is, for example, a coupling element acting as a gas removal point.

BACKGROUND

Corresponding to applicable standards, gas areas are to be separated in space—among other things, in medical technology—from electronic or electrical areas. This applies especially to medical supply units. Such a specification is based on the circumstance that, for example, an increased oxygen concentration may lead to a fire or an explosion in conjunction with electrical potentials.

To separate a gas area from electronic or electrical areas, i.e., areas with electrical and/or electronic circuits or consumers, such areas are currently partitioned either horizontally or vertically. The fact that escaping gas, for example, oxygen (O2), is heavier than air and sinks downward under the effect of the force of gravity in a partitioned area, and the gas is mixed with ambient air at the bottom of the device, for example, via a ventilation opening, is utilized in case of a horizontal partitioning of the area. Consequently, an area, which is separated from an electronic or electrical area by a horizontal partitioning plate, which is arranged under the electronic or electrical area in space, acts as a gas area. In case of a vertical partitioning of the area, a vertical partitioning plate separates the gas area from the electronic or electrical area, and escaping gas, which is heavier than ambient air, sinks downward into the partitioned area under the effect of gravity in this case as well.

Such a separation is currently brought about by ventilation openings, partition plates or completely separated ducts. ISO 11197, the particular safety standard for medical supply units, specifies in the currently verified version (status of 2004) a separation/partitioning as well as ventilation within the supply unit in order to counteract an enrichment of oxygen. ISO 11197, status of 2004, permits a nearly freely selectable positioning of gas removal points for removing combustible gases, especially $O_2$ and $N_2O$. However, ISO 11197, status of 2016, specifies, in addition to the requirements according to the 2004 status, a defined leakage of 1 L of $O_2$ per minute for an inflow time of at least 10 minutes. Free positioning of gas removal points for removing combustible gases is greatly limited hereby, since the positioning of a gas removal point is no longer possible, for example, above a power outlet by the definition of the size of the leakage. The large volume of $O_2$ ensures a rising $O_2$ value above a critical value of, for example, 25 vol. %. Permissible positionings are possible now to a limited extent only, for example, by a vertical partitioning of the area and vertical positioning (gas next to electrical area) or horizontal partitioning of the area and horizontal positioning (electrical area above gas).

SUMMARY OF THE INVENTION

One object of the present invention is to provide a device by means of which fire and/or explosion hazards based on escaping gas can be avoided with certainty, and especially to provide a possibility of positioning gas removal points essentially freely while avoiding fire and/or explosion hazards.

This object is accomplished according to the present invention by means of a gas-tight sealing device. The gas-tight sealing device includes a sealing device portion to enclose at least one part of a coupling element or a part of a wall with the coupling element, on the one hand, and to enclose, on the other hand, at least one section of a line element connected to the coupling element, namely, in a gas-tight manner. For this gas-tight enclosure, the sealing device portion adjoins the line element at a first sealing point in a gas-tight manner, extending all around, and the sealing device portion adjoins at a second sealing point the coupling element or a wall in or at which the coupling element is mounted, in a gas-tight manner extending all around. The sealing device portion encloses a volume defined by the geometry of the sealing device in a gas-tight manner between the first sealing point and the second sealing point.

The coupling element is a device for passing on an arriving gas stream into a line element that can be connected to the coupling element. For example, a pipe connection in the form of a tube connection bushing acts as a coupling element, the line element being connected to a section intended for inserting an end of the line element. The line element is intended and set up for passing on the gas stream, and the line element is, for example, a flexible tube or the like.

The advantage of the present invention is that the sealing device portion with the sealing device portion volume between the first sealing point and the second sealing point collects gas possibly escaping between the line element and the coupling element and encloses the line element and the coupling element in a gas-tight manner. A fire or explosion hazard due to escaping gas is thus avoided with certainty, since gas flowing out cannot enter the area of electrical or electronic circuits or consumers. Based on the fact that avoidance of the fire and explosion hazard is achieved, a coupling element acting as a gas removal point can be positioned, in principle, as desired, i.e., for example, also in the vicinity in space of electrical or electronic circuits or consumers. This facilitates the construction of devices, for example, medical devices, especially medical devices in the form of medical supply units, which comprise at least one gas removal point, and it makes possible, for example, a more compact structural shape, because no special distance has to be maintained between a gas removal point and electrical or electronic circuits or consumers.

In one embodiment of the gas-tight sealing device, the sealing device portion is manufactured in one piece with the first sealing point and the second sealing point from a material acting as a seal at the sealing point edges, for example, from an elastomer. The resulting flexibility of the sealing device portion facilitates the handling and mounting thereof. The one-piece configuration avoids the use of an otherwise necessary seal and thus likewise facilitates the handling and mounting.

In another embodiment of the gas-tight sealing device, the sealing device portion has a vent port between the first sealing point and the second sealing point. A pressure equalization between the interior of the sealing device and the surrounding area as well as removal of gas collected by means of the sealing device are possible via the vent port. A line element in the form of a flexible tube or the like may be connected to the vent port in order to release the gas collected during a removal at a location at which the gas would not cause any fire or explosion hazard.

In a special embodiment of the gas-tight sealing device, the sealing device portion is configured geometrically and in terms of construction in such a manner that a compact structural shape requiring only a small volume will be obtained. Provisions are made for this for the sealing device portion not to enclose any additional components aside from the coupling element or the part of the coupling element as well as the part of the line element. The walls of the sealing device portion can thus tightly adjoin the outer surfaces of the coupling element and of the line element. Such a compact structural shape leads to a gas removal point with a surrounding sealing device portion requiring only an insignificantly larger space for installation of the of the gas-tight sealing device than a gas removal point without such a of the gas-tight sealing device. This facilitates the construction of devices, especially medical devices with at least one gas removal point enclosed by means of a gas-tight sealing device with a sealing device portion of the type here and hereinafter described.

Another aspect of the invention comprises a medical device, especially a medical device acting as a medical supply unit, with at least one coupling element and with a line element connected to the coupling element, wherein at least one part of the coupling element as well as at least one section of the line element are enclosed by means of a gas-tight sealing device with a sealing device portion of the type here and hereinafter described.

An exemplary embodiment of the present invention will be explained below in more detail. Mutually corresponding objects or elements are designated by the same reference numbers in all figures.

The exemplary embodiment shall not be considered to represent a limitation of the present invention. Variations and modifications, especially such variants and combinations that the person skilled in the art can find with respect to accomplishing the object by a combination or variation of individual features described in connection with the general or special part of the description as well as contained in the claims and/or in the drawings and that lead to a new process or object through combinable features, are within the scope of the present disclosure.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
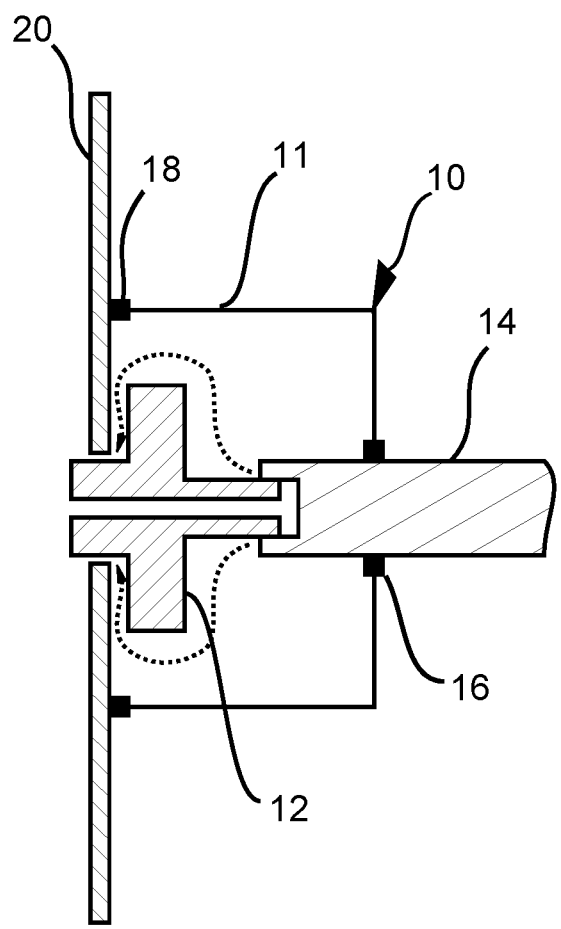
FIG. 1 is a schematic view showing a gas-tight sealing device that surrounds a coupling element as well as a tube section and encloses same with gas-tight sealing.

Referring to the drawings, the view in FIG. 1 shows an embodiment of a particular a gas-tight sealing device generally designated 10, shown in a schematically simplified sectional view. The gas-tight sealing device 10 comprises a sealing device portion (a wall/barrier that is gas impermeable) 11, which gas-tightly encloses a coupling element 12 acting, for example, as a removal point (gas removal point) for combustible gas, especially a coupling element 12 in the form of or configured as a tube connection bushing, as well as a section of a line element 14 connected to the coupling element 12, i.e., for example, a section of a flexible tube. The gas-tight sealing device 10 adjoins for this the line element 14, extending all around in a gas-tight manner, at a first sealing point (sealing edge) 16, and the gas-tight sealing device 10 comprises for this, for example, a seal, which is in contact with the outer surface of the line element 14 in the area of the first sealing point 16 in a manner that is known, in principle, per se, and thus ensures a gas-tight closure. The gas-tight sealing device 10 likewise adjoins at a second sealing point (sealing edge) 18, extending in a gas-tight manner all around, either the coupling element 12 or, as is shown here, a wall 20, for example, a housing wall, a building wall or the like, namely, a wall 20, in or at which the coupling element 12 is mounted. Here as well, the gas-tight sealing device 10 comprises, for example, a seal, which is in contact with the surface of the wall 20 in the area of the second sealing point 18, in a manner known, in principle, per se. Instead of a seal in the area of the first and/or second sealing point 16, 18, the gas-tight sealing device 10 may also be gas-tightly connected to the line element 14 or to the coupling element 12 or to the wall 20 with the first and/or second sealing point 16, 18 comprising a bonded connection. Such bonded connection sealing points (bonded sealing edges) 16, 18 have the advantage that the sealing points 16, 18 are also effective directly for fixing the sealing device portion 11 as a whole in a stationary manner. An additional mechanical fixation of the sealing device portion (sealing device wall) 11, which maintains the sealing device portion in position, i.e., in a gas-tight contact with, for example, the wall 20, may possibly also be necessary in case of a seal at the first and/or second sealing point 16, 18.

The gas-tight sealing device 10 brings about a gas-tight enclosure of the connection point between the line element 14 and the coupling element 12. In case of a mounted gas-tight sealing device 10, the gas being discharged in case of a leaky connection of the line element 14 to the coupling element 12 reaches only the interior of the gas-tight sealing device 10. The gas can possibly flow off from there possibly via remaining gaps between the coupling element 12 and the wall 20, as this is shown in the view in FIG. 1 by the arrows originating from the end of the line element 14, which end is connected to the coupling element 12.

Figure 2:
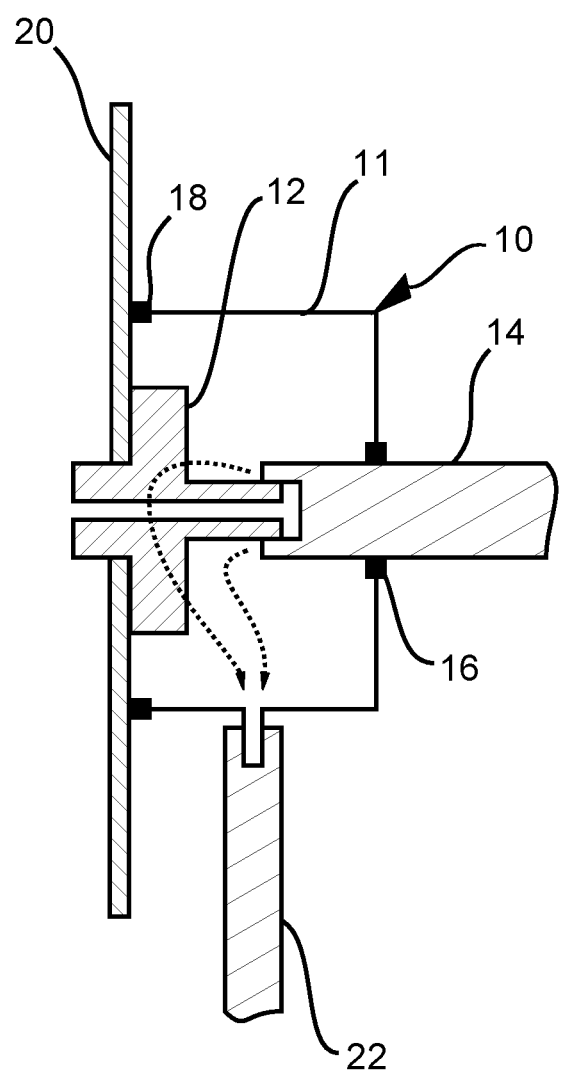
FIG. 2 is a schematic view showing the sealing device according to FIG. 1 with a removing line element connected to the sealing device portion.

The view in FIG. 2 shows an embodiment of the gas-tight sealing device 10 according to FIG. 1, in which this has a vent port for a removing/vent line element, which will hereinafter be called a flexible tube 22 for distinction from the line element 14, but without abandoning a continued general validity. Gas that is discharged to the coupling element 12 in case of a leaky connection of the line element 14 to the coupling element 12 and first enters the interior of the sealing device 10 can flow off via the flexible tube 22. The vent port and a possibly connected flexible tube 22 generally act as a vent of the gas-tight sealing device 10.

Figure 3:
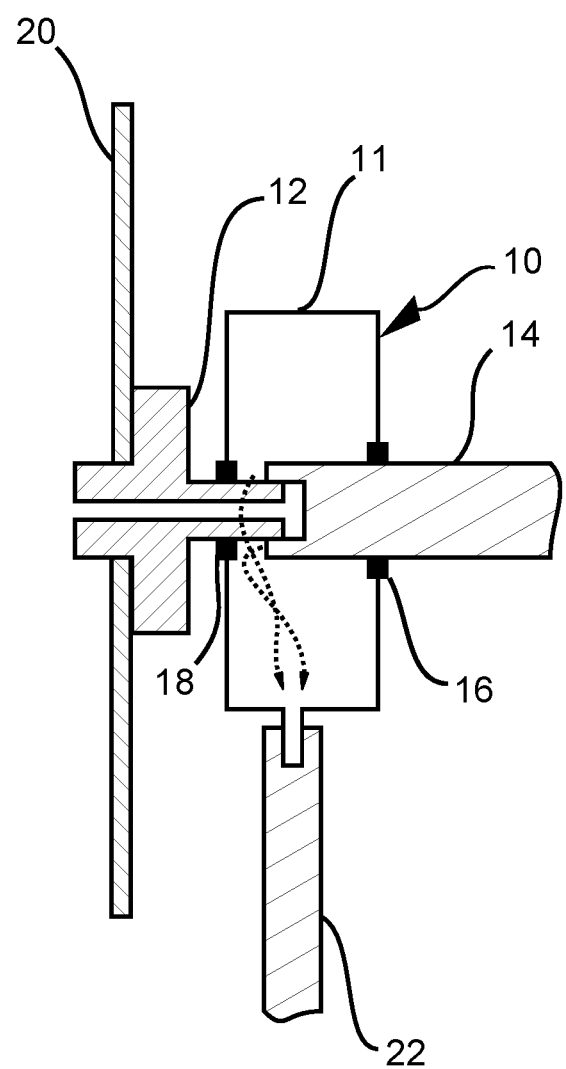
FIG. 3 is a schematic view showing a sealing device as shown in FIG. 2, wherein the gas-tight sealing device adjoins the coupling element.

The view in FIG. 3 shows an embodiment in which the gas-tight sealing device 10 is connected to the line element 14, on the one hand, and to the coupling element 12, on the other hand, and thus ensures a gas-tight enclosure of the connection point between the line element 14 and the coupling element 12. The explanations given in connection with FIG. 1 and FIG. 2 correspondingly apply to the embodiment of the gas-tight sealing device 10 shown in FIG. 3, so that unnecessary repetitions can be eliminated here. Contrary to the embodiment shown in FIG. 1 and FIG. 2, the gas-tight sealing device 10 adjoins, extending in a gas-tight manner all around, the coupling element 12 at a second sealing point 18. The gas-tight sealing device 10 adjoins, extending in a gas-tight manner all around, the line element 14 at a first sealing point 16, in a manner similar to the embodiment shown in FIG. 1 and FIG. 2.

Figure 4:
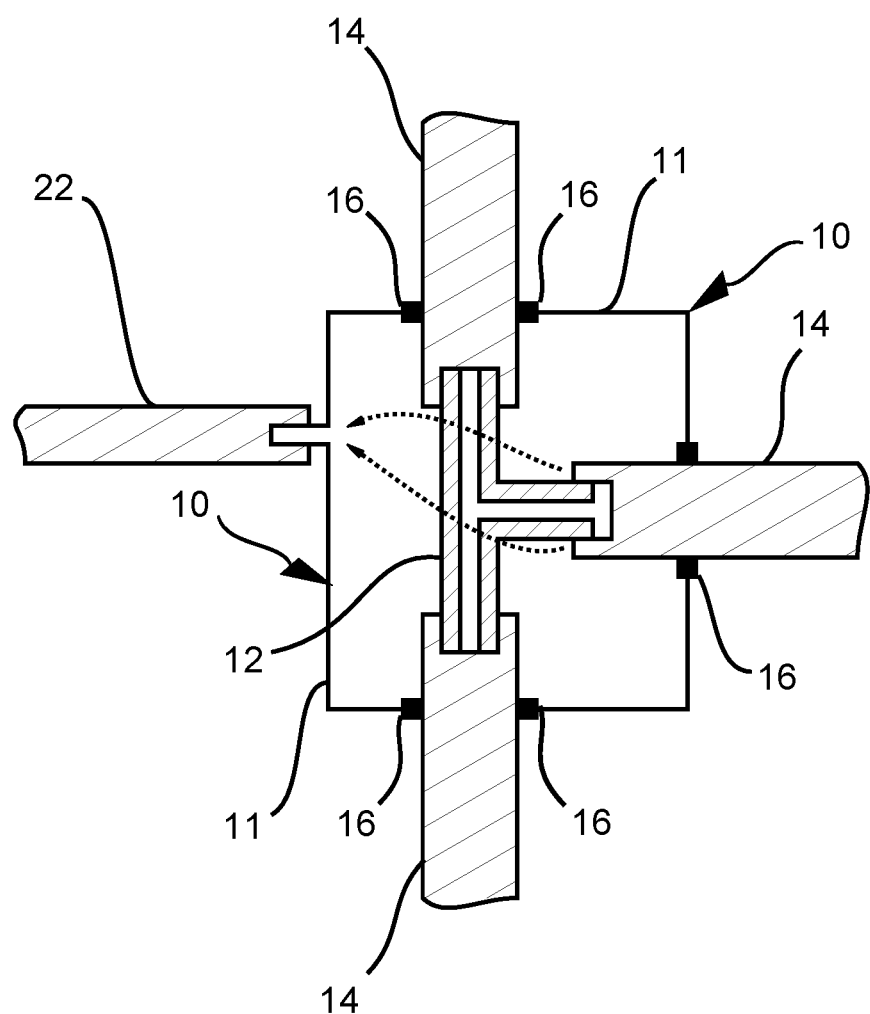
FIG. 4 is a schematic view showing a gas-tight sealing device, which surrounds a plurality of tube sections connected to the coupling element and the coupling element and encloses same with gas-tight sealing.

The view in FIG. 4 shows an embodiment, in which the gas-tight sealing device 10 encloses a plurality of connection points between a coupling element 12 and a respective line element 14 in a gas-tight manner. The gas-tight sealing device 10 has a number of sealing points (first, second, and further sealing edges) 16 corresponding to the number of line elements 14, and the gas-tight sealing device 10 adjoins, extending all around in a gas-tight manner, the respective line element 14 at these sealing points 16. In the embodiment shown, this has a basically optional vent port, and a flexible tube 22 is connected, likewise optionally, via this vent port, to the gas-tight sealing device 10 for removing gas escaping at a connection point between the coupling element 12 and a line element 14 and collected by means of the gas-tight sealing device 10.

It applies to all the embodiments shown that the respective sectional views show only one section of the wall (sealing device portion) 11 of the gas-tight sealing device 10 and that the gas-tight sealing device 10 is accordingly complemented at right angles to the drawing plane in both directions to obtain a closed housing comprised of the wall (sealing device portion) 11. The gas-tight sealing device 10 is preferably a one-piece plastic part. The gas-tight sealing device 10 is optionally elastic and is made, for example, in one piece from a material acting as a seal at the edge, for example, an elastomer. A multipart gas-tight sealing device 10 may also be provided. The gas-tight sealing device 10 has one or more sealing points with seals or bonds for a gas-tight connection of one of the individual parts to the other individual part.

The gas-tight sealing device 10 according to FIG. 1, FIG. 2 and FIG. 3 may have a cylindrical basic shape, with a vertical axis parallel to a coupling element 12 fully or partially enclosed in the gas-tight sealing device 10. As an alternative, the gas-tight sealing device 10 may also have a polygonal basic shape, for example, a cubic or cuboid basic shape. The outer shape of the gas-tight sealing device 10 is, in principle, freely selectable and may also have any desired degree of complexity, for example, in view to the smallest possible volume and hence the smallest possible space requirement, and follow, for example, the boundary lines of the respective enclosed components (coupling element 12, line element 14) encapsulated in the interior of the gas-tight sealing device 10.

The configurations according to FIG. 1 through FIG. 4 act, for example, as gas removal points. Based on the gas-tight enclosure of the connection point or of each connection point, which is/are, in principle, subject to the risk of leakage, by means of the gas-tight sealing device 10, the gas removal point as a whole is enclosed in a gas-tight manner. The gas removal point (site) may thus be positioned, in principle, as desired, and the gas removal site may also be located, for example, in the vicinity of electrical or electronic circuits or consumers.

Individual aspects of the description being filed here, which are in the foreground, can thus be briefly summarized as follows: A gas-tight sealing device 10 is provided, which comprises a sealing device portion (wall) that encloses at least one part of a coupling element 12 or a part of a wall 20 with the coupling element 12, on the one hand, as well as at least one section of a line element 14 connected to the coupling element 12, on the other hand, wherein the gas-tight sealing device 10 is connected, extending in a gas-tight manner all around, to the line element 14 at a sealing point (sealing edge) 16, wherein the sealing device 10 is connected, extending in a gas-tight manner all round, at another sealing edge 16 and/or 18 to the coupling element 12 or to a wall 20, in or at which the coupling element 12 is mounted, and wherein the sealing device portion (wall) 11 encloses a volume defined by the geometry of the gas-tight sealing device 10 in a gas-tight manner between the sealing edges (such as between the first sealing point 16 and the second sealing point 18). The sealing device 10 acts as a single partitioning device, contrary to the partitioning in individual areas, as it is provided in the current state of the art.

While specific embodiments of the invention have been shown and described in detail to illustrate the application of the principles of the invention, it will be understood that the invention may be embodied otherwise without departing from such principles.

APPENDIX

List of Reference Numbers

10 Gas-tight sealing device
11 Sealing device portion (wall/barrier)
12 Coupling element
14 Line element
16 First (and/or second) sealing point (edge)
18 Second (further) sealing point (edge)
20 Wall
22 Flexible tube (removing line element)

What is claimed is:

1. A medical device comprising:
a wall;
a coupling element mounted to the wall and configured as a gas removal point;
a line element connected to the coupling element; and
a gas-tight sealing device, wherein at least one part of the coupling element as well as at least one section of the line element are enclosed in a gas-tight manner by the gas-tight sealing device, the sealing device comprising:
a sealing device portion, which encloses at least one part of the coupling element as well as at least one section of the line element connected to the coupling element;

a first sealing point, the sealing device portion adjoining the first sealing point and extending around the line element at the first sealing point; and a second sealing point, the sealing device portion adjoining the second sealing point and extending around the coupling element, said second sealing point being connected to the wall in a gas tight manner, whereby the sealing device portion encloses a volume defined by a geometry of the sealing device portion between the first sealing point and the second sealing point.

2. A medical device in accordance with claim 1, wherein the sealing device portion, the first sealing point and the second sealing point are formed as one piece from a material acting as a seal at edges defined by the first sealing point and the second sealing point.

3. A medical device in accordance with claim 1, further comprising a vent port formed in the sealing device portion between the first sealing point and the second sealing point, said vent port being configured to connect to a vent line.

4. A medical device in accordance with claim 1, wherein the enclosed volume of the sealing device portion encloses no additional components aside from the coupling element or the part of the coupling element and the section of the line element.

5. A medical device in accordance with claim 1, wherein:
the gas-tight sealing device is configured to flow off gas from a leaky connection of the line element to the coupling element.

6. A medical device in accordance with claim 1, wherein:
the gas-tight sealing device is configured to collect gas escaping between the line element and the coupling element.

7. A medical device in accordance with claim 1, wherein:
the second sealing point is connected to a first side of the wall in a gas tight manner;
the wall and the coupling element define a gap between the wall and the coupling element, the sealing device being configured to flow off gas discharged from a leaky connection of the line element with the coupling element, the discharged gas flowing from the first side of the wall to a second side of the wall.

8. A medical device in accordance with claim 1, wherein:
the wall has a gas area and an electrical area;
the coupling element is mounted in the gas area of the wall.

9. A medical device in accordance with claim 1, further comprising:
a medical supply device, the wall being part of the medical supply device;
the coupling element being a gas removal point of the medical supply device.

10. A medical device in accordance with claim 9, wherein:
the medical supply device provides a combustible gas stream to the gas removal point;
the coupling element passes on an arriving gas stream from the medical supply device;
the line element passes on the gas stream from the coupling element.

11. A medical device comprising:
a wall;
a coupling element mounted to the wall and configured as a gas removal point;
a line element connected to the coupling element;
a sealing device wall encloses at least one part of the coupling element as well as at least one section of the line element connected to the coupling element;

a sealing edge, the sealing device wall adjoining the sealing edge and gas-tight extending around the line element at the sealing edge; and a further sealing edge connected to the wall, the sealing device wall adjoining the further sealing edge and gas-tight extending around the further sealing edge, whereby the sealing device wall encloses a volume defined by a geometry of the sealing device wall between the sealing edge and the further sealing edge in a gas-tight manner, the volume including at least one part of the coupling element as well as at least one section of the line element.

12. A medical device in accordance with claim 11, wherein the sealing edge and the further sealing edge comprise seals.

13. A medical device in accordance with claim 11, wherein the sealing edge and the further sealing edge comprise bonded edges of the sealing device wall.

14. A medical device in accordance with claim 11, wherein sealing device wall, the sealing edge and the further sealing edge are formed as one piece from a material acting as a seal at edges defined by the sealing edge and the further sealing edge.

15. A medical device in accordance with claim 11, further comprising a vent port formed in the sealing device wall between the sealing edge and the further sealing edge, said vent port being configured to connect to a vent line.

16. A medical device in accordance with claim 11, wherein the enclosed volume of the sealing device wall encloses no additional components aside from the coupling element or the part of the coupling element and the section of the line element.

17. A medical device in accordance with claim 11, wherein:
the sealing device wall is configured to flow off gas from a leaky connection of the line element to the coupling element.

18. A medical device in accordance with claim 11, wherein:
the second sealing point is connected to a first side of the wall in a gas tight manner;
the wall and the coupling element define a gap between the wall and the coupling element, the sealing device wall being configured to flow off gas discharged from a leaky connection of the line element with the coupling element, the discharged gas flowing from the first side of the wall to a second side of the wall.

19. A medical device comprising:
a wall;
a coupling element mounted in said wall, and configured as a gas removal point to pass on a gas stream from the wall;
a line element connected to said coupling element and configured to pass on the gas stream from said coupling element;
a sealing device having a first sealing edge surrounding, and connected to, said line element in a gas-tight manner, said sealing device having a second sealing edge surrounding said coupling element, said second sealing edge being connected to one of said wall and said coupling element in a gas tight manner, said second sealing edge being connected to said wall in a gas tight manner;
said wall and said coupling element defining a gap between said wall and said coupling element, said sealing device being configured to flow off gas discharged from a leaky connection of said line element with said coupling element, the discharged gas flowing from a first side of said wall to a second side of said wall.

20. A medical device in accordance with claim 19, further comprising:
   a vent port arranged in said sealing device;
   a tube connected to said vent port and having a link to a remote location, said vent port and said tube being configured to remove gas collected by said sealing device to a remote location separate from the gas stream.

* * * * *